United States Patent [19]

Kikumoto et al.

[11] 4,098,661
[45] Jul. 4, 1978

[54] METHOD OF PRODUCING NEOSCHIZOPHYLLAN HAVING NOVEL PHARMACOLOGICAL ACTIVITY

[75] Inventors: Syoichi Kikumoto, Handa; Osamu Yamamoto, Kobe; Nobuhiko Komatsu, Tokyo; Haruhiko Kobayashi, Mitaka; Teruo Kamasuka, Kodaira, all of Japan

[73] Assignees: Taito Co., Ltd.; Kaken Chemical Co., Ltd., both of Tokyo, Japan

[21] Appl. No.: 734,008

[22] Filed: Oct. 19, 1976

[30] Foreign Application Priority Data

Oct. 31, 1975 [JP] Japan .................. 50-131229

[51] Int. Cl.² ............................. B01J 1/12
[52] U.S. Cl. ................ 204/160.1; 204/158 S
[58] Field of Search .............. 204/158 S, 160.1

[56] References Cited

U.S. PATENT DOCUMENTS 4,029,616  6/1977  Nakashio et al. .............. 204/158 S

OTHER PUBLICATIONS

Journal of Polymer Science, vol. XXV, No. 110 (Aug., 1957) pp. 285–304.

*Primary Examiner*—Howard S. Williams
*Attorney, Agent, or Firm*—Oblon, Fisher, Spivak, McClelland & Maier

[57] ABSTRACT

Neoschizophyllan is produced by an ultrasonication of Schizophyllan which is extracted from a culture solution of Schizophyllum commune Fries or a fruit body thereof.

3 Claims, 3 Drawing Figures

EFFECT OF ALKALINE CONCENTRATION ON VISCOSITY
AND $[\alpha]_D^{20}$ OF NEOSCHIZOPHYLLAN

METHOD OF PRODUCING NEOSCHIZOPHYLLAN HAVING NOVEL PHARMACOLOGICAL ACTIVITY

BACKGROUND OF THE INVENTION

The present invention relates to Neoschizophyllan of a novel polysaccharide and the process for producing Neoschizophyllan.

Neoschizophyllan can be obtained by an ultrasonication of Schizophyllan.

Schizophyllan is a polysaccharide having antitumor and antibacterial action which can be obtained by extracting and purifying a culture solution of Schizophyllum commune Fries which belongs to Basidiomycetes or a fruit body thereof.

The structure, manufacture and antitumor action of Schizophyllan have been disclosed in GANN 60, p. 137 to 144 (1969) and Japanese Journal of Antibiotics 26, p. 277 to 283 (1973) and U.S. Pat. No. 3,943,247 as well understood the structure, manufacture and antitumor action of Schizophyllan. Accordingly, in the specification, the description is not recited and the disclosures should be considered those of U.S. Pat. No. 3,943,247 and the journals.

Schizophyllan has excellent antitumor action as disclosed in the prior arts, however, Schizophyllan is sparingly soluble in water and an aqueous solution of Schizophyllan has high viscosity. Accordingly, when orally administered, the absorption of the Schizophyllan is very poor, whereby the antitumor action is not substantially found.

In order to give desired therapeutic effect, it is necessary to administrate a large amount of a dilute solution of Schizophyllan and accordingly, it is difficult to administrate Schizophyllan to human body by an injection.

In the subcutaneous injection or the intramuscular injection of Schizophyllan, the local pain and induration are caused. In the intravenous injection of Schizophyllan, the occlusion of blood-vessel and other troubles are caused in the circulatory system.

Accordingly, Schizophyllan could not be used as a medicine.

SUMMARY OF THE INVENTION

It is an object of the invention to provide a novel polysaccharide of Neoschizophyllan which has low viscosity in the form of an aqueous solution and which can be applicable for therapeutic purpose.

Another object of the invention is to provide a novel polysaccharide of Neoschizophyllan which has low toxicity as an injectable solution.

The object of the invention is to provide a novel polysaccharide of Neoschizophyllan which can be absorbed by an oral administration.

These objects of the present invention have been attained by an ultrasonication of Schizophyllan.

DETAILED DESCRIPTION OF THE EMBODIMENTS

Figure 1:
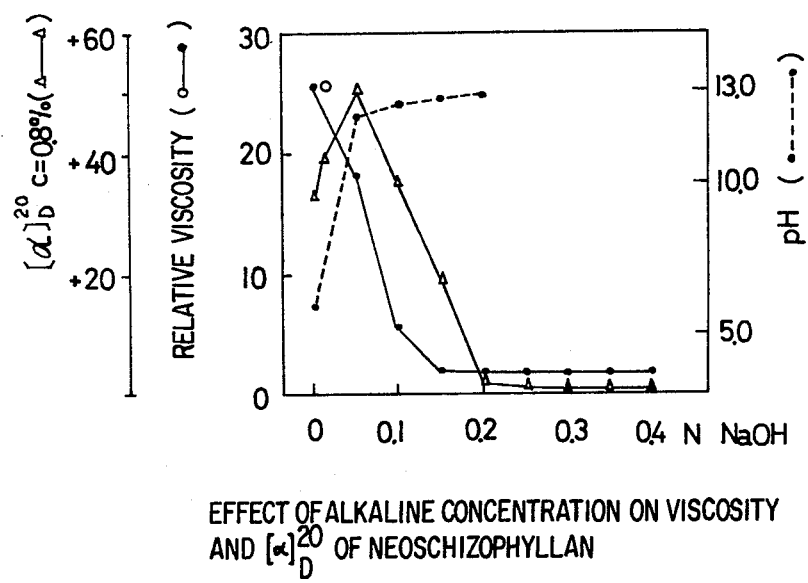

In order to obtain polysaccharides having antitumor effect without the above-mentioned disadvantages, the inventors have studied many derivatives and degraded products of Schizophyllan. As the result, novel degraded product of polysaccharide which has not the above mentioned disadvantages and has pharmacological activity which is the same or higher than that of Schizophyllan and has low toxicity and low viscosity in a form of an aqueous solution can be obtained by the ultrasonic treatment of Schizophyllan. The novel polysaccharide is called as Neoschizophyllan in the nomenclature. According to the analysis of the ultracentrifugation, the gel filtration and high voltage electrophoresis, Neoschizophyllan gave a single peak whereby it was confirmed to be a homogenous compound.

The basical structure of Neoschizophyllan is considered as the same with that of Schizophylan as shown in the formula I.

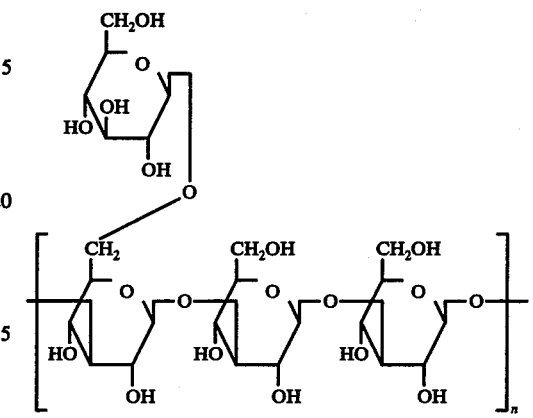

The molecular weight of Neoschizophyllan varies depending upon the methods of measurement as those of polymers.

In accordance with the Park-Johnson method, the molecular weight of Schizophyllan is 20,000 to 60,000 while the molecular weight of Neoschizophyllan is 1,500 to 4,000.

In accordance with the ultracentrifugation Schlierene pattern method, the molecular weight of Schizophyllan is 150,000 to 2500,000 while the molecular weight of Neoschizophyllan is 300,000 to 700,000.

The pharmacological properties of Neoschizophyllan are remarkably different from those of Schizophyllan.

The toxicity of Neoschizophyllan is remarkably low comparing with those of Schizophyllan. For example, $LD_{50}$(i.v.) of Schizophyllan is 30 mg/kg whereas $LD_{50}$(i.v.) of Neoschizophyllan was 718 mg/kg.

As shown in the following Test 1, the optimum dose of Schizophyllan is more than 2 mg/kg whereas the optimum dose of Neoschizophyllan is less than 2 mg/kg for showing the best effect.

When Schizophyllan is chemically or enzymatically degraded with an acid or an enzyme, the pharmacological effect is decreased and in most cases, homogenous degraded product could not be obtained.

Accordingly, Neoschizophyllan is quite different from the degraded products produced by the chemical or enzymatic methods.

The physical properties of Neoschizophyllan are as follows.
1. White powder, no taste, no smell:
2. Basical structure: (stated above)
3. Molecular weight: (stated above).

In the Park-Johnson method, the condition of treatment for the measurement is severe whereby the molecules are cut in the treatment for measurement to increase the reducing terminals so as to be measured as smaller molecular weight. In the ultracentrifugation-Schlieren Pattern method, each molecular weight was given by the following equation <Mandelkern-Flory equation, J. Chem. Phys. 20, 212 (1952)>.

$$M = \left[ \frac{S_{20, w}[\eta]^{1/3}\eta o\, N}{\beta (1 - \bar{v}P)} \right]^{3/2}$$

$N = 6.023 \times 10^{23}$
$\eta$ = intrinsic viscosity
  Schizophyllan 13 dl/g
  Neoshizophyllan 6.45 dl/g
$\eta o = 0.01005$ poise
$\bar{v} = 0.55$ ml/g (estimation)
$\rho = 0.998$ g/ml
$S_{20}$, w; (See paragraph 8)
$\beta$; 2.16 to 2.4 $\times 10^6$ (estimation)

4. Elementary analysis: No nitrogen: C/H ratio is about 6/1.
5. Intrinsic viscosity; 1 to 6 (dl/g); (Schizophyllan : 12 to 15 dl/g)
6. Relative viscosity; See FIG. 1.
7. $[\alpha]_D^{20}$: See FIG. 1.
8. Sedimentation coefficient: $S_{20,w}$ 3 to 7 (Schlieren pattern); (Schizophyllan 10 to 13)
9. NMR:
   Proton-decoupled C-13 NMR spectrum of Neoschizophyllan (sonicated time 10 hrs.) at room temp. in alkali solution (0.5 N) (100 mg/2.5 ml).

Width 4,000 Hz, 8K data points, 26,190 accumulations, cyclic time 1.5 sec., pulse angle 45°.

| No. | PPM | Height(%) |
|---|---|---|
| 1 | 104.331 | 12.165 |
| 2 | 103.938 | 9.735 |
| 3 | 87.551 | 4.156 |
| 4 | 87.083 | 5.682 |
| 5 | 77.173 | 16.462 |
| 6 | 75.965 | 4.858 |
| 7 | 74.442 | 19.147 |
| 8 | 71.049 | 9.607 |
| 9 | 70.113 | 5.347 |
| 10 | 69.369 | 12.122 |
| 11 | 61.997 | 15.595 |

Reference:
  Proton-decoupled C-13 NMR spectrum of Schizophyllan at room temp. in alkali solution (0.5 N) (100 mg/2.5 ml).

Width 4,000 Hz, 8K data points, 35,963 accumulations, cyclid time 1.5 sec., pulse angle 45°.

| No. | PPM | Height(%) |
|---|---|---|
| 1 | 104.368 | 17.768 |
| 2 | 103.981 | 11.981 |
| 3 | 87.629 | 7.745 |
| 4 | 87.161 | 10.132 |
| 5 | 77.173 | 21.790 |
| 6 | 75.965 | 8.337 |
| 7 | 74.520 | 23.231 |
| 8 | 71.086 | 10.645 |
| 9 | 69.410 | 17.115 |
| 10 | 61.957 | 20.618 |

10. Color reaction:
   Negative for Iodine reaction; Positive for Molish, Phenolsulfuric acid, and Anthrone reactions:
11. Solubility:
   One gram of Neoschizophyllan is completely dissolved in 9 ml of water after 10 minutes of stirring at room temperature whereas Schizophyllan remains undissolved even after 1 hour of stirring in the same condition.
12. $LD_{50}$(mouse)

|  | Neoschizophyllan | Schizophyllan |  |
|---|---|---|---|
| i.v. | 718 mg/kg | 30 mg/kg | |
| i.p. | >2000 mg/kg | >250 mg/kg | it is impossible to give large dose. |
| i.m. | >100 mg/kg | — | |
| s.c. | >2000 mg/kg | — | |
| p.o. | >1000 mg/kg | — | |

The ultrasonication of the invention will be illustrated. It has been known to convert polymers to compounds having lower molecular weight by the ultrasonication.

The ultrasonication of dextran has been studied by M. Stacey and the ultrasonication of starch, agar, sodium alginate, chondroitin sulfuric acid and methyl cellulose has been studied by many researchers. [A. R. Lockwood et al., Research Supplement 4-I, Pages 46 to 48 (1951); M. Stacey ibid. page 48 (1951); A. Otsuka et al., Yakuzai gaku Vol. 26, pages 203 to 207 and 207 to 210 (1966); T. Tatsuhara and S. Iguchi ibid. Vol. 32, pages 86 to 95 (1972)].

In the prior arts, the changes of viscosity and molecular weight of polymers by the ultrasonication and the mechanism of the ultrasonication have been discussed, however, the pharmacological activities and clinical toxicities of the products or the by-products have not been discussed.

It is possible to dissolve Schizophyllan in a hydrophylic organic solvent such as dimethylformamide and dimethylsulfoxide before the ultrasonication, however, it is preferable to dissolve it in water from the viewpoint of the use of the product.

The ultrasonication can be carried out in various conditions.

The output of the ultrasonication can be given by the equation:

$$W = 2\pi^2 \rho C (FA)^2$$

wherein
  W: output per unit area
  $\rho$: density of solution
  C: velocity of sound in solution
  F: frequency
  A: amplitude.

In the ultrasonication, the concentration of the solution of Schizophyllan is usually higher than 0.1 wt.% preferably higher than 0.5 wt.% When the concentration of Schizophyllan is high, Schizophyllan is not dissolved and the viscosity is high to decrease the effect of the ultrasonication. Accordingly, it is usually less than 5 wt.%.

In the ultrasonication, it is preferable to give a large amplitude i.e., 5 to 500 microns especially 10 to 200 microns under the frequency of 5 to 50 KHz preferably 8 to 30 KHz. It is preferable to give higher amplitude though a corrosion of a vibrating plate and other trouble of the apparatus may be considered in high amplitude. Wehn the frequency is too low, a noise is caused whereas when the frequency is too high, a desired amplitude cannot be given.

In the ultrasonication, the total output energy is usually 0.1 to 50 watt-hour per 1 cc especially 0.5 to 10 watt-hour per 1 cc of the solution of Schizophyllan. When the concentration of Schizophyllan is low, the total output energy can be lower.

It is preferable to recycle the solution in the ultrasonication so that the solution is uniformly contacted with the vibrating plate.

In the ultrasonication, it is preferable to select the shape of the vessel so as to efficiently and uniformly contact the molecules of Schizophyllan with the surface of the vibrating plate or to equip a desired stirrer.

The optimum conditions are dependent upon the concentration of Schizophyllan, the oscillating frequency, the output, the shape and size of the vessel and the stirrer. In usual, when 2 liters of 1.5% Schizophyllan solution is treated by the ultrasonication, it is enough to apply it at 500 W for 6 to 8 hours. When the amount of the solution and the concentration of Schizophyllan are increased, the time for ultrasonication may be prolonged proportional to the increases. When suspending particles are contained in the solution, the attenuation of energy should be considered. The time for ultrasonication should be prolonged when the stirring is not enough or bubbles are included into the solution.

When the energy of ultrasonication is too low, it is not enough to convert Schizophyllan to Neoschizophyllan whereby Schizophyllan and the poorly degraded Schizophyllan are remained. In the medical use, it is not always necessary to separate them when the amounts of the remained Schizophyllan and the poorly degraded Schizophyllan are small.

FIG. 1 is a graph showing the effect of the alkaline concentration of the viscosity and $[\alpha]_D^{20}$ of Neoschizophyllan. When the concentration of NaOH is higher than 0.1N, the relative viscosity and $[\alpha]_D^{20}$ are remarkably decreased. When the concentration of NaOH is higher than 0.2N, the relative viscosity and $[\alpha]_D^{20}$ are quite low.

Figure 2:
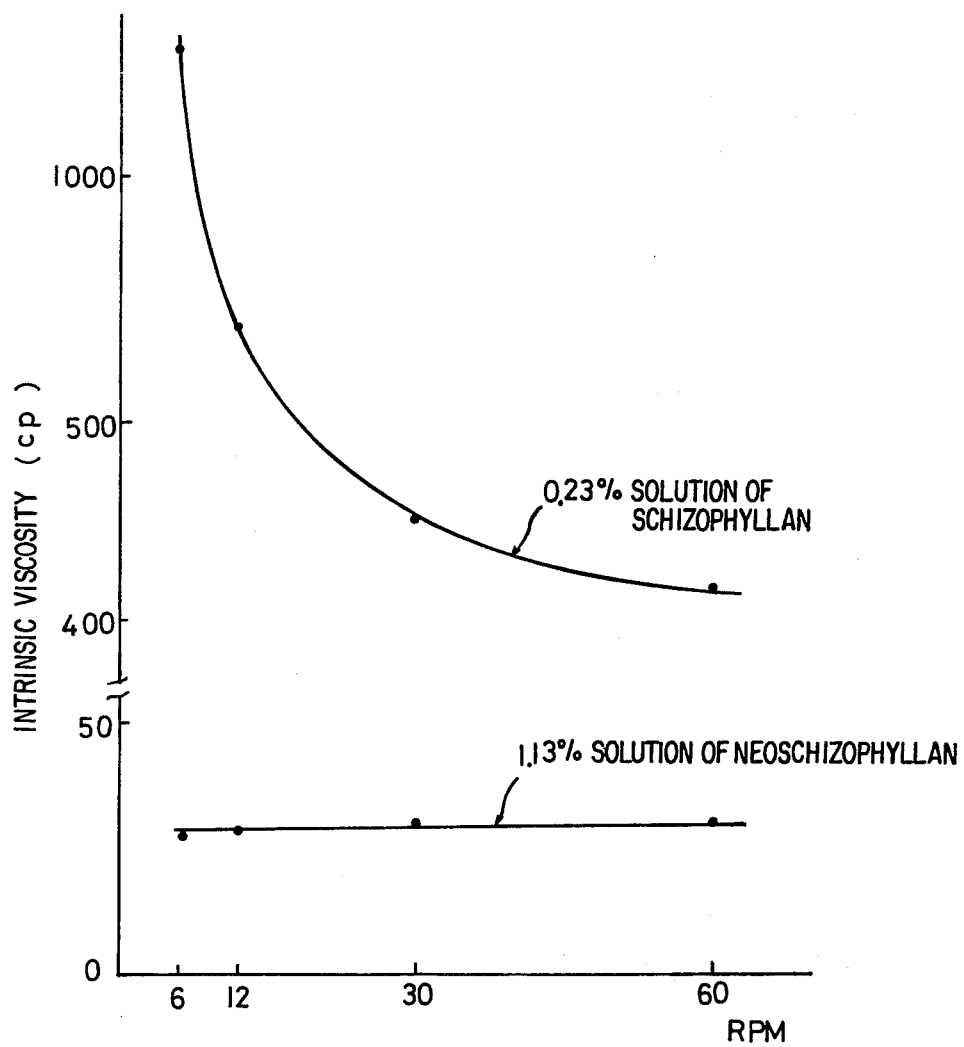

FIG. 2 is a graph showing the viscosity characteristics of the solutions of Schizophyllan (0.23%) and Neoschizophyllan (1.13%) (Intrinsic viscosity-rotary speed r.p.m.).

The membrane filtration must be carried out for a preparation of a medicine.

The characteristics of filtrations of Schizophyllan and Neoschizophyllan through a millipore filter are shown in Table 1.

The other advantages of the invention is to be able to prepare a solution having high concentration of Neoschizophyllan.

A maximum concentration of a solution of Schizophyllan is about 0.4% whereas it is easy to prepare 3 – 5% solution of Neoschizophyllan in the preparation of a medicine without any difficulty.

It is possible to prepare a medical solution having low viscosity and high concentration by using Neoschizophyllan, whereby the above-mentioned disadvantages of Schizophyllan in the preparation of a medicine can be satisfactorily prevented.

The most important advantage of the invention is to give a novel compound of Neoschizophyllan which has a pharmacological activity comparable to or even higher than that of Schizophyllan and has remarkably low toxicity.

Neoschizophyllan is absorbed into blood and tissues more rapidly than Schizophyllan.

Neoschizophyllan can also be used as an intermediate for various derivatives.

Neoschizophyllan of the invention can be administered by various methods such as oral administration, subcutaneous injection, an intramuscular injection and an intravenous injection.

Neoschizophyllan can be dosed in any desired form such as a tablet, a capsule, an injectable solution, a syrup, and the other pharmaceutical compositions.

Neoschizophyllan can be combined with the other antitumor medicine such as Mitomycin C, 5-Fluorouracil, 6-Mercapropurine, Cytosine-arabinoside, Bleomycin, etc.

A dosage of Neoschizophyllan is usually 0.005 to 100 mg/kg/day, preferably 0.05 to 2 mg/kg/day. A concentration of the injectable solution is preferably 0.05 to 4%.

Table 1

| | Characteristics of filtration by Millipore filter: | | | |
|---|---|---|---|---|
| | Concentration of solution | Time for filtering 1 liter of solution | Number of sheets of membranes used | Filtering velocity |
| No treatment | 0.05 % | 4.0 hour | 3 | 83 ml/hr/cm² |
| | 0.10 % | 10.0 hour | 4 | 33 ml/hr/cm² |
| | 0.15 % | difficult | — | — |
| Ultra-sonification | | | | |
| | 0.5 % | 1 hour | 0 | 330 ml/hr/cm² |
| | 1.0 % | 2.5 hour | 2 | 132 ml/hr/cm² |
| | 1.5 % | 4.0 hour | 3 | 83 ml/hr/cm² |
| | 2.0 % | 10.0 hour | 5 | 33 ml/hr/cm² |

Note:
Area of filtration 3.0 cm³
Membranes pretreatment membrane (AP 25), DA(0.65μ) HA (0.45μ), and the filtration at the same time.

The graph shows that the solution of Neoschizophyllan had low viscosity and was Newtonian liquid though the solution of Schizophyllan had high viscosity and was non-Newtonian liquid. The changes of the viscosity and Newtonian property are irreversible.

Figure 3:
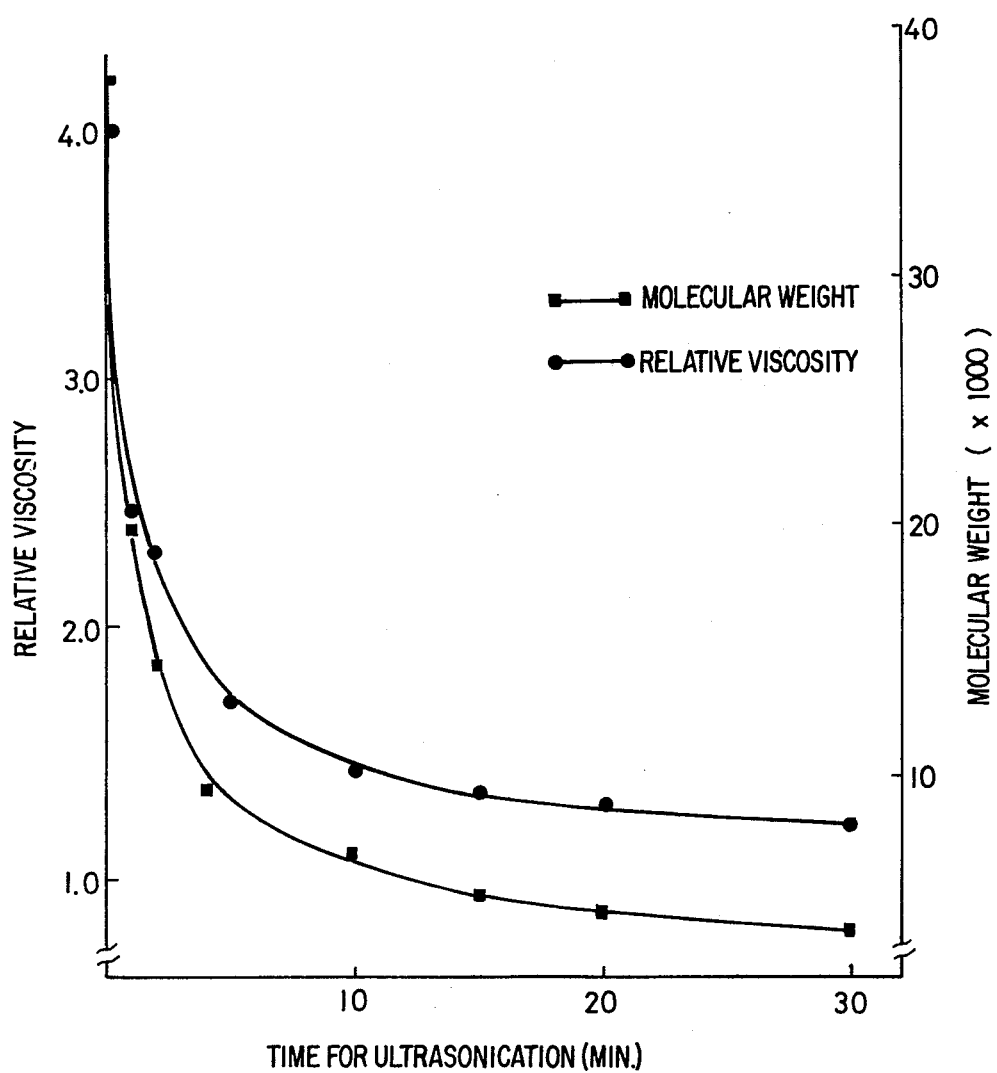

FIG. 3 shows the time course of changes in relative viscosity and molecular weight in the ultrasonication (the molecular weight of the product was measured by the Park-Johnson method). (0.1% Schizophyllan aqueous solution).

One of the advantages of the invention is to easily perform a membrane filtration of Neoschizophyllan.

The invention will be further illustrated by certain examples.

EXAMPLE 1

A 500 mg of polysaccharide of Schizophyllan powder which was produced by extracting and purifying a culture solution of Schizophyllum Commune Fries was completely dissolved in 500 ml of a hot water.

The solution of Schizophyllan was treated by the ultrasonication at the oscillating frequency of 20 KHz in an amplitude of 20 microns and the output of 100 W with stirring the solution so as to uniformly contact with the vibrating plate without incorporating bubbles.

After the ultrasonication for 60 minutes, the solution of Neoschizophyllan having the following properties was obtained.

The pharmacological activity of Neoschizophyllan was substantially the same with that of Schizophyllan.

| Intrinsic viscosity | 3.5 (dl/g) |
| --- | --- |
| Relative viscosity | 1.5 |
| Molecular weight | |
| Park-Johnson method | 2,500 |
| Ultracentrifugal method | 420,000 |
| Sedimentation coefficient | 5.3 |

EXAMPLE 2

A 10 g of Schizophyllan powder of Example 1 was dispersed in 2 liters of water and the dispersion was heated at 120° C for 20 minutes and then it was stirred to dissolve it by the Warning blender.

The solution was treated by the ultrasonication at the oscillating frequency of 20 KHz in an amplitude of 35 microns and the output of 1 KW at room temperature with stirring.

After the ultrasonication for 30 minutes under confirming the decrease of the viscosity, 10 g of Schizophyllan powder was further added and dispersed in the solution and the dispersion was further treated by the ultrasonication in the same condition.

The operation was repeated for further two times to dissolve 40 g of Schizophyllan in the solution.

After dissolving all of Schizophyllan, the solution was treated by the ultrasonication in the same condition for 6 hours, to obtain 2% of a solution of Neoschizophyllan having the following properties.

The solution had Newtonian flow characteristics as the viscosity characteristic measured by Brookfield viscometer.

According to the tests, the pharmacological activity of the solution of Neoschizophyllan was slightly higher than that of Shizophyllan and the toxicity of the solution of Neoschizophyllan was remarkably lower than that of Schizophyllan.

| Intrinsic viscosity | 5.2 (dl/g) |
| --- | --- |
| Relative viscosity | 310 |
| Molecular weight | |
| Park-Johnson method | 3,800 |
| Ultracentrifugal method | 650,000 |
| Sedimentation coefficient | 6.7 |

EXAMPLE 3

A 10 g of Schizophyllan powder of Example 1 was dissolved in 1 liter of water and the solution was treated by the ultrasonification at the room temperature at the oscillating frequency of 30 KHz in an amplitude of 8 microns and the output of 500 W with stirring the solution.

After the ultrasonication for about 4 hours, the solution of Neoschizophyllan having the following properties was obtained.

| Intrinsic viscosity | 2.3 (dl/g) |
| --- | --- |
| Relative viscosity | 80 |
| Molecular weight | |
| Park-Johnson method | 1,800 |
| Ultracentrifugal method | 320,000 |
| Sedimentation coefficient | 3.4 |

EXAMPLE 4

A 100 g of Schizophyllan powder of Example 1 was dissolved in 2 liters of water and the solution was treated by the ultrasonication at the room temperature at the oscillating frequency of 8 KHz in an amplitude of 450 microns and the output of 2 KW with stirring the solution.

After the ultrasonication for about 6 hours, the solution of Neoschizophyllan having the following properties was obtained.

| Intrinsic viscosity | 4.2 (dl/g) |
| --- | --- |
| Relative viscosity | 880 |
| Molecular weight | |
| Park-Johnson method | 2,800 |
| Ultracentrifugal method | 480,000 |
| Sedimentation coefficient | 5.5 |

EXAMPLE 5

A 20 g of Schizophyllan powder of Example 1 was dissolved in 1 liter of water and the solution was treated by the ultrasonication at the room temperature at the oscillating frequency of 8 KHz in an amplitude of 100 microns and the output of 500 W with stirring the solution.

After the ultrasonication for about 7 hours, the solution of Neoschizophyllan having the following properties was obtained.

| Intrinsic viscosity | 4.8 (dl/g) |
| --- | --- |
| Relative viscosity | 250 |
| Molecular weight | |
| Park-Johnson method | 3,200 |
| Ultracentrifugal method | 580,000 |
| Sedimentation coefficient | 6.2 |

COMPARATIVE TEST 1

The process of Example 3 was repeated without stirring.

After the ultrasonication for 2 hours, Schizophyllan was adhered at the end of the vibrating plate in dry condition by heating, and the ultrasonication efficiency was remarkably low.

After the ultrasonication, the lowering of the viscosity was found only around the vibrating plate. When the solution was mixed in the stage, the gel having the following properties which was similar to the solution before the ultrasonication was formed.

| Intrinsic viscosity | 9.3 (dl/g) |
| --- | --- |
| Molecular weight | |
| Park-Johnson method | 28,000 |
| Ultracentrifugal method | 1100,000 |
| Sedimentation coefficient | 9.3 |

COMPARATIVE TEST 2

The process of Example 5 was repeated with vigorously stirring under incorporating bubbles.

After the ultrasonication for 7 hours and 13 hours, the solution had the following properties because of bubbles.

|  | after 7 hours | after 13 hours |
|---|---|---|
| Intrinsic viscosity | 7.8 (dl/g) | 4.6 (dl/g) |
| Relative viscosity | — | 265 |
| Molecular weight | | |
| Park-Johnson method | 11,000 | 3,400 |
| Ultracentrifugal method | 950,000 | 540,000 |
| Sedimentation coefficient | 8.5 | 6.1 |

TEST 1

The antitumor effect of Neoschizophyllan on Sarcoma 180 tumor was compared with that of Schizophyllan.

The test was carried out by the method stated in GANN, 60, p. 137 to 144 (1969).

The solution was given to mice by the intramuscular injection for 10 times once every 2 days 24 hours after the transplantation of tumor. The results are shown in Table 2.

As it is clear from the data of Table 2, Neoschizophyllan had the same effect as that of Schizophyllan. The optimum dosage of Neoschizophyllan was clearly different from that of Schizophyllan.

Table 2

| | Dosage mg/kg × times<br>Number of mice | 0.05 × 10<br>20 | 0.1 × 10<br>20 | 0.2 × 10<br>20 | 0.5 × 10<br>20 | 1.0 × 10<br>20 |
|---|---|---|---|---|---|---|
| Increase of Body Weight | Group of Neoschizophyllan | 5.8 | 3.9 | 4.6 | 4.4 | 3.0 |
| | Group of Schizophyllan | 5.8 | 3.8 | 3.1 | 3.9 | 3.1 |
| | Control | 7.9 | 4.1 | 7.9 | 4.4 | 3.6 |
| Tumor inhibition ratio | Group of Neoschizophyllan | 41.2 | 71.4 | 81.5 | 97.0 | 97.9 |
| | Group of Schizophyllan | 10.1 | 62.0 | 73.1 | 80.3 | 89.9 |
| No. of mice tumor disappeared | Neoschizophyllan | 2 | 2 | 4 | 11 | 10 |
| | Schizophyllan | 0 | 1 | 2 | 4 | 10 |

TEST 2

In accordance with the method of Example 8 of U.S. Pat. No. 3,943,247, the test of the treatment of tuberculosis was carried out with Neoschizophyllan and Schizophyllan.

The effect of Neoschizophyllan was substantially equal to that of Schizophyllan though the optimum dosage was different as shown in Test 1.

What is claimed is:

1. A process for producing Neoschizophyllan which comprises treating a solution or a dispersion of Schizophyllan by a ultrasonication at a frequency of 5 to 50 KHz with stirring without incorporating bubbles.

2. A process according to claim 1, wherein said ultrasonication is applied with an amplitude of 5 to 500 microns.

3. A process according to claim 1, wherein said ultrasonication is applied at a frequency of 8 to 30 KHz.

* * * * *